United States Patent
Kugel et al.

(12) 
(10) Patent No.: US 6,280,453 B1
(45) Date of Patent: *Aug. 28, 2001

(54) HERNIA MESH PATCH WITH STIFFENER LINE SEGMENT

(75) Inventors: Robert D. Kugel, Olympia, WA (US); J. Douglas Inman, Arlington; Keith D. Biggers, Southlake, both of TX (US)

(73) Assignee: Bard Asdi Inc., Murray Hill, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,224

(22) Filed: Feb. 11, 1999

Related U.S. Application Data

(63) Continuation-in-part of application No. 09/006,653, filed on Jan. 14, 1998, now Pat. No. 5,916,225, which is a continuation of application No. 08/755,108, filed on Nov. 22, 1996, now Pat. No. 5,769,864, which is a continuation-in-part of application No. 08/315,249, filed on Sep. 29, 1994, now Pat. No. 5,634,931.

(51) Int. Cl.$^7$ .................................................. A61B 17/04
(52) U.S. Cl. ............................... 606/151; 602/44; 602/58
(58) Field of Search ........................... 606/157, 213–215, 606/110, 113; 602/44, 58

(56) References Cited

U.S. PATENT DOCUMENTS

| | | | |
|---|---|---|---|
| 2,671,444 | 3/1954 | Pease, Jr. | 606/151 |
| 3,054,406 | 9/1962 | Usher | 606/151 |
| 4,007,743 | 2/1977 | Blake . | |
| 4,347,847 | 9/1982 | Usher | 606/151 |
| 4,452,245 | 6/1984 | Usher | 606/151 |

(List continued on next page.)

FOREIGN PATENT DOCUMENTS

| | | |
|---|---|---|
| 2114282 | 7/1994 | (CA) . |
| 0 362 113 | 4/1990 | (EP) . |
| 0 474 887 | 10/1991 | (EP) . |
| 676 285 | 7/1979 | (SU) . |
| 782 814 | 11/1980 | (SU) . |
| WO 90/14796 | 12/1990 | (WO) . |
| WO 93/17635 | 9/1993 | (WO) . |
| WO 94/27535 | 12/1994 | (WO) . |
| WO 96/09795 | 4/1996 | (WO) . |
| WO 97/22310 | 6/1997 | (WO) . |

OTHER PUBLICATIONS

Gregory L. Brown, M.D. et al., "Comparison of Prosthetic Materials for Abdominal Wall Reconstruction in the Presence of Contamination and Infection", Annals of Surgery, Jun. 1985, vol. 201, pp. 705–711.

(List continued on next page.)

Primary Examiner—Gary Jackson
(74) Attorney, Agent, or Firm—Wolf, Greenfield & Sacks, P.C.

(57) ABSTRACT

A hernia patch has a first layer of inert synthetic mesh material selectively sized and shaped to extend across and beyond a hernia. A second layer of inert synthetic mesh material overlies the first layer to create a generally planar configuration for the patch. The first and second layers are joined together by a seam that defines a periphery of a pouch between the layers. One or both of the layers has a border that extends beyond the seam. A plurality of border slits extend from an outer edge of the border through the border substantially to the seam. An access slit is formed between the layers for insertion of a finger of a surgeon into the pouch to allow the surgeon to deform the planar configuration of the patch to facilitate insertion of the patch into the patient and to position the patch across the hernia. A resilient monofilament spring is located within the pouch at the seam for urging the patch to conform to the generally planar configuration across the hernia as the surgeon withdraws his or her finger.

12 Claims, 2 Drawing Sheets

U.S. PATENT DOCUMENTS

| | | |
|---|---|---|
| 4,561,434 | 12/1985 | Taylor . |
| 4,633,873 | 1/1987 | Dumican et al. .................... 606/151 |
| 4,655,221 | 4/1987 | Devereux .............................. 606/151 |
| 4,693,720 | 9/1987 | Scharnberg et al. ................. 606/151 |
| 4,710,192 | 12/1987 | Liotta et al. ............................. 623/1 |
| 4,769,038 | 9/1988 | Bendavid ............................... 623/13 |
| 4,796,603 | 1/1989 | Dahlke . |
| 4,854,316 | 8/1989 | Davis . |
| 4,865,026 | 9/1989 | Barrett . |
| 4,955,907 | 9/1990 | Ledergerber . |
| 5,006,106 | 4/1991 | Angelchik . |
| 5,059,205 | 10/1991 | El-Nounou et al. . |
| 5,116,357 | 5/1992 | Eberbach ............................... 606/151 |
| 5,122,155 | 6/1992 | Eberbach ............................... 606/151 |
| 5,141,515 | 8/1992 | Eberbach ............................... 606/151 |
| 5,147,374 | 9/1992 | Fernandez ............................. 606/151 |
| 5,147,384 | 9/1992 | La Rocca . |
| 5,147,387 | 9/1992 | Jansen ....................................... 623/1 |
| 5,176,692 | 1/1993 | Wilk et al. ............................. 606/151 |
| 5,192,301 | 3/1993 | Kamiya et al. ....................... 606/213 |
| 5,195,542 | 3/1993 | Gazielly et al. ...................... 128/898 |
| 5,201,745 | 4/1993 | Tayot et al. ........................... 606/151 |
| 5,254,133 | 10/1993 | Seid . |
| 5,258,000 | 11/1993 | Gianturco . |
| 5,290,217 | 3/1994 | Campos . |
| 5,334,217 | 8/1994 | Das ....................................... 606/151 |
| 5,350,399 | 9/1994 | Erlebacher et al. . |
| 5,356,432 | 10/1994 | Rutkow et al. ....................... 606/151 |
| 5,366,460 | 11/1994 | Eberbach . |
| 5,368,602 | 11/1994 | de la Torre . |
| 5,370,650 | 12/1994 | Jovey et al. . |
| 5,397,331 | 3/1995 | Himpens et al. . |
| 5,425,744 | 6/1995 | Fagan et al. . |
| 5,433,996 | 7/1995 | Kranzler et al. . |
| 5,451,235 | 9/1995 | Lock et al. . |
| 5,456,720 | 10/1995 | Schultz et al. . |
| 5,507,811 | 4/1996 | Koike et al. . |
| 5,593,441 | 1/1997 | Lichtenstein et al. . |
| 5,614,284 | 3/1997 | Kranzler et al. . |
| 5,695,525 | 12/1997 | Mulhauser et al. . |
| 5,702,416 | 12/1997 | Kieturakis et al. . |
| 5,716,408 | 2/1998 | Eldridge et al. . |
| 5,743,917 | 4/1998 | Saxon . |
| 5,766,246 | 6/1998 | Mulhauser et al. . |
| 5,769,864 | 6/1998 | Kugel . |
| 5,824,082 | 10/1998 | Brown . |
| 5,836,961 | 11/1998 | Kieturakis et al. . |
| 5,879,366 | 3/1999 | Shaw et al. . |
| 5,916,225 | 6/1999 | Kugel . |
| 5,919,232 | 7/1999 | Chaffringeon et al. . |
| 5,922,026 | 7/1999 | Chin . |
| 5,954,767 | 9/1999 | Pajotin et al. . |

OTHER PUBLICATIONS

Scott D. Jenkins, M.D. et al., "A Comparison of Prosthetic Materials Used to Repair Abdominal Wall Defects", Surgery, Aug. 1983, vol. 94, No. 2, pp. 392–398.

"Prevention of Postsurgical Adhesions by Interceed (TC7)", Fertility and Sterility, Jun. 1989, vol. 51, No. 6, pp. 933–938.

Hernando Cordona, M.D., "Prosthokeratoplasty", 1983, Cornea, vol. 2, No. 3, 1983, pp. 179–183.

Alonzo P. Walker, M.D., et al. "Double–Layer Prosthesis for Repair of Abdominal Wall Defects in a Rabbit Model", pp. 32–37, Journal of Surgical Research, vol. 55, No. No. 1, Jul. 1993.

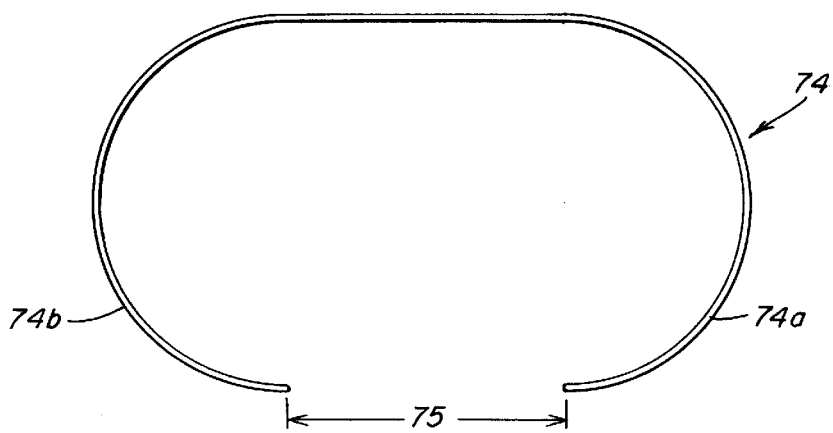
Fig. 4
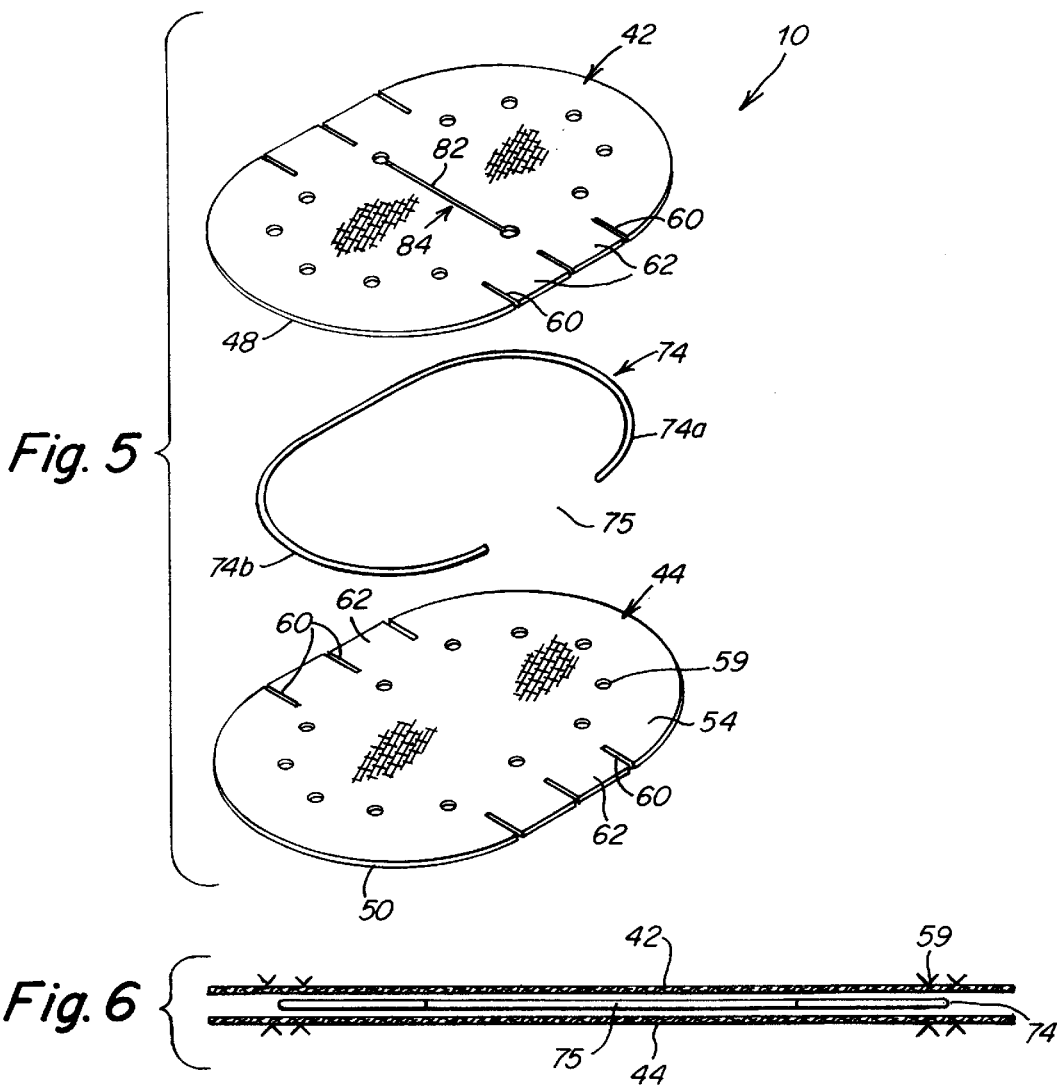
Fig. 5
Fig. 6

HERNIA MESH PATCH WITH STIFFENER LINE SEGMENT

CROSS-REFERENCE TO RELATED APPLICATION

This application is a continuation-in-part of patent application Ser. No. 09/006,653, filed Jan. 14, 1998, now U.S. Pat. No. 5,916,225, which was a continuation of application Ser. No. 08/755,108, Nov. 22, 1996, now U.S. Pat. No. 5,769,864, which is a continuation-in-part of application Ser. No. 08/315,249, Sep. 29, 1994, now U.S. Pat. No. 5,634,931.

TECHNICAL FIELD

The present invention generally relates to a surgically implantable patch for use in repairing a hernia of other aperture in a human body. More particularly, the present invention relates to a hernia repair patch having a filament to stiffen and maintain the patch in a planar configuration.

BACKGROUND OF THE INVENTION

Surgically implantable mesh patches for the repair of inguinal and other abdominal wall hernias, which are intended for permanent placement within a patient's body space, have been provided and used previously. Tension free surgical repairs of hernias have been developed using synthetic mesh materials to bridge and to patch hernia defects. These repairs resulted in both a decrease in the recurrence rate as well as a decrease in the amount of a patient's post operative discomfort. Patients undergoing these more advanced procedures were able and are able to resume their normal activities sooner.

Some of the earlier techniques are somewhat complicated. Several use a plug or a locating member to fit within the hernia defect itself. Also, many of the earlier techniques were designed specifically for use in laparoscopic repair of hernias. Moreover, many of the prior inventions required suturing to the patient's body tissue. Although these medical advances are acknowledged for their usefulness and success, a need remains for improvements in the surgical repair of hernias.

DISCLOSURE OF INVENTION

A hernia mesh patch for use in the surgical repair of a patient's inguinal, or other abdominal wall hernias, is disclosed for permanent placement within a patient's body space. The hernia mesh patch of the invention has top and bottom layers of an inert, synthetic mesh, preferably polypropylene mesh, secured to each other with a seam. The seam is preferably formed by an ultrasonic weld that surrounds a stiffener or spring.

To serve a spring function, an inert monofilament fiber, arranged in a partial oval, ovoid, loop, or ring configuration, is affixed between a top layer and a bottom layer of the hernia mesh patch to keep the hernia mesh patch expanded under tension in a planar configuration. An opening is formed in one of the layers for allowing a surgeon to insert a finger. The opening allows the surgeon to properly position the patch. A border on at least one of the layers extends outward past the seam. The border preferably has slits, which form tabs that fill uneven voids in the patient's tissue.

Without the need for general anesthesia, nor expensive laparoscopic instrumentation, a surgeon makes a small incision in the patient when repairing an inguinal hernia. The small incision is preferably approximately three centimeters long, arranged obliquely, and located approximately two to three centimeters above the internal ring location of the inguinal hernia. Through this small incision, using the muscle splitting technique, the surgeon performs a dissection deep into the patient's preperitoneal space to create a pocket in the space into which the hernia mesh patch is to be inserted.

Thereafter, the surgeon uses his or her fingers to fold and compact the hernia mesh patch and direct the patch through the incision and into the patient's preperitoneal space, where the patch unfolds and expands into its planar configuration, creating a trampoline effect. The surgeon then places one of his or her fingers through the opening between the top and bottom layers of the hernia mesh patch to conveniently and accurately move the hernia mesh patch to cover the defect in the thick reinforcing lining of a patient's abdominal cavity. Thereafter, the surgeon withdraws his or her finger and secures the incision with stitches.

Soon after surgery, the patient's body reacts to the mesh of the hernia mesh patch. In a short time the mesh becomes stuck, thereby keeping the hernia mesh patch in place. Thereafter, the patient's scar tissue grows into the mesh over a period of time, typically between thirty and sixty days, to permanently fix the hernia mesh patch in its intended position over the repaired area where the hernia was located.

DESCRIPTION OF DRAWINGS

FIG. 4 is a top view of an alternate embodiment of a resilient monofilament spring of the invention.

FIG. 5 is an exploded view of the surgically implantable hernia repair mesh patch shown in FIGS. 2 and 3 that shows the two layers of the mesh and also the alternate embodiment of the resilient monofilament spring shown in FIG. 4.

FIG. 6 is a transverse cross sectional view of the center of the preferred surgically implantable hernia repair mesh patch, illustrated in FIGS. 2 and 3, with the top and bottom layers shown slightly separated for illustrative purpose.

BEST MODE FOR CARRYING OUT THE INVENTION

Figure 1:
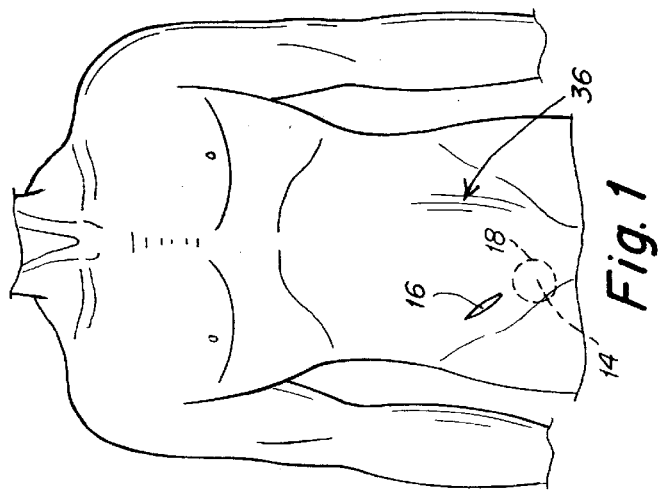
FIG. 1 is a schematic partial front view of a patient's body, which indicates a repair location of an inguinal hernia.
Figure 2:
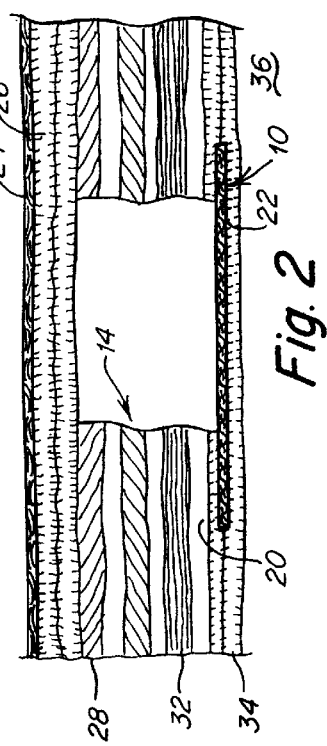
FIG. 2 is a schematic partial diagrammatic cross-sectional view of a patient's abdominal wall layers showing an inguinal or other abdominal wall hernia, with a hernia repair mesh patch positioned in the preperitoneal created space.

The hernia mesh patch 10, illustrated in the drawings, is surgically permanently implantable within a patient's body space to adequately cover, correct, prevent and repair any inguinal or other abdominal wall hernias 14 or other types of hernias. The surgeon has the objective of making a sutureless repair by first cutting an approximately three centimeter incision 16, obliquely positioned approximately two to three centimeters above the location described as the internal ring 18, as shown in FIG. 1.

The surgeon then works through incision 16 and uses a muscle splitting technique to dissect deeply into the patient's preperitoneal space 20. The surgeon enters slightly superior and posterior to the patient's hernia defect 14. The surgeon uses a sharp instrument to make the incision 16 through the patient's skin 24, the subcutaneous fatty tissues 26, and the external oblique fascia 28, which has been cut parallel with its fibers a short distance. The surgeon then incises the transversalis fascia 32, creating an entrance into the preperitoneal space 20 above the peritoneum 34 at a location proximate to the hernia 14. In so doing, the surgeon identifies and frees up the hernia sac and creates the pocket 22 in the preperitoneal space 20. Space 20 underlies the area referred to as Hesselbach's triangle, in reference to both indirect and direct hernias. The surgeon's placement of the hernia mesh patch 10 in accordance with this method protects the entire inguinal floor. Therefore, not only will the patch 10 repair or correct a single small hernia, but will also protect against future hernias through other potentially weakened areas.

In a similar way, a hernia mesh patch 10 is sandwiched between a hernia defect 14 and the inner lining or peritoneum 34 of the abdominal cavity 36 to underlay a femoral canal area, not shown, through which femoral hernias occasionally occur. Wherever used to patch and to bridge a hernia 14, the hernia mesh patch 10 serves as the basis for tension free surgical repair of the hernia 14. After completing the preparation, the surgeon uses his or her fingers to fold and compact the hernia mesh patch 10 and to insert the patch 10 down through the incision 16 into the preperitoneal space 20. Thereafter, the surgeon uses his or her finger to expand, move, and direct the hernia mesh patch 10 into position in the pocket 22 within the preperitoneal space 20 to bridge the hernia 14.

Figure 3:
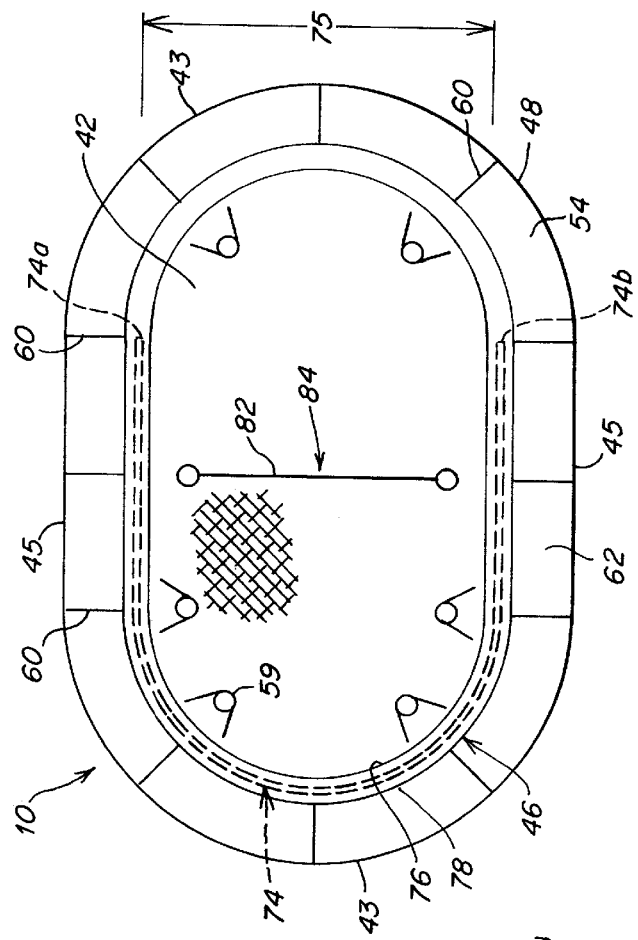
FIG. 3 is a top view of a preferred embodiment of the surgically implantable hernia repair mesh patch.

One embodiment of hernia mesh patch 10 is shown in FIGS. 3, 5 and 6. Patch 10 is composed of two similarly shaped pieces of an inert synthetic mesh material, such as a polypropylene material. The two pieces are top layer 42 and a bottom layer 44. The mesh material is formed from monofilament material that is resistant to infection, and which has been used safely in many hernia operations, in previous ways and in previous embodiments. Preferably, the two pieces of mesh material 42, 44 are made in respective circle, loop, ovoid, or oval shapes. Layers 42, 44, are secured to each other by seam 46, which is preferably formed ultrasonically. Seam 46 is approximately one centimeter in from outer edge 48 of top layer 42 and outer edge 50 of bottom layer 44 in an embodiment wherein top layer 42 is the same size as bottom layer 44.

The outer one centimeter of mesh material of either or both of the top and the bottom mesh material piece or layers 42 and 44 is left free to serve as a border or apron 54 to fill uneven voids in the patient's tissue. When the hernia mesh patch 10 has been placed in the preperitoneal space, border 54 serves to frictionally keep patch 10 in the appropriate repair position. Inside of the seam 46, like size darts 59 (FIGS. 3 and 6), may be positioned respectively in the top and/or bottom mesh layers 42, 44. The presence of darts 59 helps initially to frictionally keep the hernia mesh patch 10 in place. Thereafter, the patient's scar tissues grow in and around darts 59 to continue to keep the hernia mesh patch in position. The outer one centimeter of layers 42 and 44 may have cuts or slits 60 formed radially or diagonally, which create scalloped or fringed edges or tab portions 62 on the outer one centimeter of the top and bottom mesh layers 42, 44.

A spring 74, made of a synthetic material, such as nylon, polypropylene, or polyester is positioned between the layers 42 and 44. Layers 42, 44 are attached together at points closely surrounding the spring 74. Spring 74 is not a closed loop in this embodiment. Rather, it has two ends 74a, 74b that are spaced from each other creating a gap 75. The circumferential length of gap 75 is less than the circumferential length of spring 74. If desired, seam 46 may also have two ends that terminate at gap 75 (FIG. 3) or they may extend completely in an oval loop as shown in FIG. 3. A monofilament line forms spring 74. Prior to placement between layers 42, 44, spring 74 may be a straight line that is bent into a desired shape, such as a half loop. Seam 46 captivates spring 74. Seams 76, 78 are located inward from the outer edge of layer 42. In the embodiment of FIG. 3, patch 10 is oval having two curved ends 43 and two straight sides 45. Opening 75 is located at one of the curved ends.

The top mesh material, or top layer piece 42, may be cut to form an access slit 82 transversely at the center thereof, creating a finger access into the interior space or pouch 84 between the top and bottom layers 42, 44 of the synthetic mesh material. If seam 46 is terminated at the filament ends 74a, 74b, slit 82 may be eliminated, as the access opening to panels 84 could be between ends 74a, 74b. In the embodiment of FIG. 5, opening 75 between ends 74a, 74b is at one of the straight sides.

In use, at the conclusion of the surgeon's use of both sharp and blunt instruments to create pocket 22 in the preperitoneal space 20, the surgeon selects the type and size of the hernia mesh patch 10 best suited to be used in the repair of the patient's defect or hernia 14. Hernia mesh patch 10 is folded and further compacted, as may be necessary, by the surgeon using his or her fingers, so the patch 10 may be conveniently inserted through the incision 16 and down into the preperitoneal space 20.

In the repair of other hernias, and especially those that are large, a direct incision is made. After the placement of a large hernia mesh patch, the surgeon may use limited sutures to keep the larger hernia mesh patch in place. Generally, most of the embodiments of the hernia mesh patch are positioned, and so remain, without the use of sutures.

The utilization of the embodiments of hernia mesh patches have numerous advantages. Hernia patches are simple to manufacture and to insert in the surgical method of the invention. The patches adequately underlay a hernia or defect, with a minimum of two centimeters of a surrounding underlay about the circumference of the hernia. The patches maintain sufficient rigidity and sufficient friction to eliminate or minimize sliding or migration. When the hernia mesh patches are used by a surgeon, the repair of a patient's inguinal hernia or of another abdominal wall hernia is accomplished through a small incision, with less surgical tension, less post-operative patient discomfort, shorter operation time, and at a potentially lower cost to the patient. The patient's post-operative discomfort is decreased, and risk of any recurrence is likewise decreased.

While the invention has been shown in several embodiments, it should be apparent that it is not limited to those embodiments but is susceptible to various changes without departing from the scope of the invention.

What is claimed is:

1. A tissue aperture repair patch for implanting within a patient, comprising:

at least one layer of inert synthetic mesh material sized and shaped to extend across and beyond a tissue aperture in a patient;

a resilient support member adjacent a periphery of the layer and configured in an open loop to urge the layer into a planar configuration, said support member carried by the layer so as to remain implanted with the layer in the patient; and the layer of inert synthetic mesh material having a periphery extending beyond the support member that defines a border having a free outer edge to fill uneven voids in a patient's tissue.

2. The patch according to claim 1 wherein the support member is comprised of monofilament fiber.

3. The patch according to claim 1, further comprising a seam between said layers that restrains said resilient support member in said configuration.

4. The patch according to claim 1 wherein said resilient support member has two ends that are spaced apart from each other by a gap.

5. The patch according to claim 1 wherein:

said line has two ends that are spaced apart from each other by a gap; and wherein said line has a length greater than a length of said gap.

6. A tissue aperture repair patch for implanting in a patient, comprising:

a first layer of inert synthetic mesh material sized and shaped to extend across and beyond a tissue aperture in a patient;

a second layer of inert synthetic mesh material secured to the first layer to create a pouch between the first and second layers;

an opening in the pouch for providing access to an interior of the pouch to position the patch across the tissue aperture; and a resilient support member adjacent a periphery of the pouch and configured in an open loop to cause the layers to assume a flat shape, the support member being carried by the layers so as to remain implanted with the layers in the patient.

7. The patch according to claim 6, wherein:

the support member is a monofilament fiber located within the pouch.

8. The patch according to claim 6, further comprising a seam between said layers that restrains said resilient support member in said configuration.

9. The patch according to claim 6 wherein said resilient support member has two ends that are spaced apart from each other by a gap.

10. The patch according to claim 6 wherein:

said support member has two ends that are spaced apart from each other by a gap; and wherein said support member has a length greater than a length of said gap.

11. The patch according to claim 6, wherein:

the opening in the pouch comprises a slit in one of the first layer and the second layer.

12. A tissue aperture repair patch, comprising:

a first layer of inert synthetic mesh material sized and shaped to extend across and beyond a tissue aperture;

a second layer of inert synthetic mesh material overlying the first layer to create a generally planar configuration for the patch;

the first and second layers being joined together by a seam which defines a pouch between the layers;

an opening in one of the layers that enables insertion of a finger of a surgeon into the pouch to facilitate insertion of the patch into the patient and to position the patch across the tissue aperture; and a resilient support member located within the pouch and adjacent to the seam for urging the patch to conform to the generally planar configuration across the tissue aperture as the surgeon withdraws his or her finger, said resilient support member being a monofilament fiber loop having a curved portion, said resilient support member restrained in a configuration of an open loop by said seam.

* * * * *